United States Patent [19]
Kübler et al.

[11] Patent Number: 5,529,903
[45] Date of Patent: Jun. 25, 1996

[54] EXTRACTION AND CULTIVATION OF TRANSFORMED CELLS AND PRODUCTION OF ANTIBODIES DIRECTED AGAINST THEM

[75] Inventors: Ulrich Kübler, Munich; Rainer Hoffman, Fürstenfeldbruck, both of Germany

[73] Assignee: Dr. Ulrich Kübler GmbH, Germany

[21] Appl. No.: 111,520

[22] Filed: Aug. 25, 1993

[30] Foreign Application Priority Data

Aug. 26, 1992 [DE] Germany .......................... 42 28 389.2

[51] Int. Cl.$^6$ .......................... G01N 33/574; G01N 33/53
[52] U.S. Cl. .................. 435/7.23; 435/7.24; 435/240.21; 436/63; 436/64
[58] Field of Search .......................... 435/240.21, 7.23, 435/7.24; 436/63, 64

[56] References Cited

U.S. PATENT DOCUMENTS 5,112,298  5/1992  Prince et al. .................. 604/6

FOREIGN PATENT DOCUMENTS

WO89/05657  6/1989  WIPO.
WO89/07445  8/1989  WIPO.

OTHER PUBLICATIONS

C. A. K. Borrebaeck, *J. Immunol. Meth.*, vol. 123, pp. 157–165, 1989.
Hamdy et al., "Circulating Prostate Specific Antigen–Positive Cells Correlate with Metastatic Prostate Cancer," *British Journal of Urology*, 69, 392–396, (1992).
West, M. D. et al., "Tumor Embolization in Man, Studies of Cancer Cells in the Blood," *Progress in Clinical Pathology*, 3, 362–382, (1970).
Hollmann et al., "New Frontiers in Mammary Pathology 1986," *Developments in Oncology*, 49, 251–271, (1986).
Ohsako et al., "Analysis of Various Antigens in Golden Hamster Testis by Monoclonal Antibodies," *J. Vet. med. Sci.*, 53 6, 969–974, (1991). (Medline Abstract).
Ware et al., "Human, Rat or Mouse Hybridomas Secrete High Levels of Monoclonal Antibodies Following Transplantation into Mice with Severe Combined Immunodeficiency Disease (SCID)," *J. Immunol. Methods*, 85 2, 353–361, (1985). (Medline Abstract).
Kang et al., "Production and Characterization of Monoclonal Antibodies Against an Avain Group A Rotavirus," *Avain Dis*, 35 3, 563–571, (1991). (Medline Abstract).
SundarRaj, et al., "Cell–Surface Associated Proteins of Corneal Fibroblasts: Dissection with Monoclonal Antibodies," *J. Cell Biochem*, 21 4, 277–287, (1983). (Medline Abstract).
Essani, et al., "Anti–Idiotypic Antibodies Against a Human Multiple Organ–Reactive Autoantibody. Detection of Idiotopes in Normal Individuals and Patients with Autoimmune Diseases.," *J Clin Invest*, 76 4, 1649–1656 (1985). (Medline Abstract).
J. A. Fleming, et al., "A critical and comparative study of methods of isolating tumour cells from the blood", J. clin. Path (1967), 20, 145–151.
John T. West, M.D. et al., "Tumor Embolization in Man", Progress in Clinical Pathology (1970), pp. 362–382.

*Primary Examiner*—Toni R. Scheiner
*Attorney, Agent, or Firm*—Finnegan, Henderson, Farabow, Garrett, & Dunner

[57] ABSTRACT

A process is described with which it is possible without the addition of chemicals or other additives safely to extract from a living individual transformed cells and individual-specific polyclonal or mono-clonal antibodies which are directed against tumor-specific antigens on these transformed cells for diagnostic and therapeutic purposes.

12 Claims, No Drawings

EXTRACTION AND CULTIVATION OF TRANSFORMED CELLS AND PRODUCTION OF ANTIBODIES DIRECTED AGAINST THEM

The invention concerns a process for the extraction of transformed cells from the blood stream of a human or animal individual, a process for cultivating the cells thus obtained and the production of monoclonal antibodies which are directed against these cells.

Concerning the significance of transformed cells circulating in the blood stream for the formation of metastases, A. J. Salsbury reports in "Significance of Circulating Cancer Cells", William Heinemann Medical Books New Aspects of Breast Cancer, Vol. 3, pages 245 et seq., 1977, that these cancer cells circulating in the bloodstream may still not form any metastases in a period of up to 5 to 6 hours after their release—for example by certain operative and therapeutic measures. The presence of large amounts of cancer cells alone is not yet enough for the appearance of metastases, the cancer cells would first have to leave the vascular zone. Nevertheless, the use of agents is proposed which on the one hand impede the formation of thrombi as the starting points for the formation of metastases from the blood stream and on the other hand, they should kill the transformed cells.

More recent knowledge (P. M. Gullino, Dev. Oncol., 49, 251 to 271 (1986)), however, makes it clear that circulating tumor cells in most cases appear in the bloodstream long before the primary tumor can be proven clinically. Even if not all of the transformed cells are in a position to initiate metastases, it is necessary to combat the propagation of circulating tumor cells and therefore the growth of metastases as early as possible. The reason why until now no clear correlation could be established between the number of transformed cells in the peripheral blood and the initiation of metasase formation is due to a large extent to the difficulty of proving the transformed cells in the bloodstream.

Furthermore it is known that when using the conventional diagnostic processes, such as the palpating of the solid tumor, and especially in the case of bioptic and operative treatments, the release of transformed tumor cells is clearly increased, which may lead to an increased metastase formation.

The behaviour of solid tumors in the formation of metastases via the lymphatic and/or circulation system has until now only been studied in vivo in opened blood vessels during operations. Circulating tumor cells in a volume which is diagnostically or even therapeutically exploitable were not obtained. The behaviour of solid tumors in the formation of metastases in the circulatory system could therefore only be examined in tests on animals or in human beings only post mortem by the pathologist.

One is aware of a number of processes for the extraction of transformed cells from blood: chemical or enzymatic lysis of non-transformed cells, accelerated sedimentation of red blood cells, flotation, centrifugation and magnetic separation processes etc. (see the survey by J. A. Fleming and J. W. Stewart, Journal of Clinical Pathology, 20, 145–151 (1967), and J. T. West and R. H. Hume, Progress in Clinical Pathology, Vol. 3, chapter 11, 362–382 (1970)). The known methods usually lead only to small yields and they also show in particular the defect that one is not able to determine whether a transformed cell from the peripheral circulatory system was vital or not at the time of its extraction. Nevertheless, recourse is still made until today to these methods.

Transformed cells accordingly can be extracted with a density gradient centrifugation, such as is normally used for example for the isolation of lymphocytes in a Ficoll®, silicon, or albumin gradient. For this purpose, however, large amounts of blood are necessary, which is a great burden on the patient. Furthermore, despite the high cost for apparatus, the yield is extremely low based on the small number of transformed cells, which in addition are easily damaged and impurified by the conventional centrifugation process. Therefore a density gradient centrifugation process is not usable as a routine for the extraction of larger quantities of transformed cells. Recycling of the other blood components, such as plasma and red blood corpuscles, to the patients is not practicable because of impurities caused by the gradient material. The centrifugation processes are not suitable for clinical application to the patients.

Therefore until now no process which is reproducible and simple to carry out existed, which made it possible to extract by non-surgical means transformed metastasized cells which are possibly circulating in the peripheral circulatory system, to cultivate them outside the body and use them for further investigations and other applications.

The invention is based on the object of making available a process with which it is possible by simple and safe means to extract transformed cells which are circulating in the blood stream from a human or animal individual.

Connected therewith is the object of reproducing the cells thus obtained in culture and producing monoclonal antibodies directed against antigens on their surface, which can then be used for diagnostic and/or therapeutic purposes.

The invention is based on the recognition that in the case of separation of whole blood in an apheretic device which is suitable for this purpose, vital transformed cells are enriched in a fraction which still contains leucocytes and/or lymphocytes.

Thus the object is therefore achieved by a process for the isolation and cultivation of transformed cells which circulate in the blood stream, in that one withdraws from the blood with an apheretic device which is suitable for separating into blood components a fraction which is enriched with the transformed cells, which still contains leucocytes and/or lymphocytes, and reproduces the transformed cells.

To produce the individually specific antibodies which are directed against tumor antigens, one brings the cultivated transformed cells into contact with B-lymphocytes, in order to stimulate the production of antibodies directed against tumor antigens on the transformed cells, immortalizes them, reproduces them and selects the stimulated B-lymphocytes and isolates and purifies the antibodies from the immortalized B-lymphocyte culture. The antibodies thus obtained may be polyclonal or preferably monoclonal.

In principle the organism would be in a position to produce the "pharmaceutical", i.e. the antibodies, itself by its immune system. However, the number of transformed cells circulating in the blood stream and therefore the number of the corresponding antigens is in general much too low in the early stage which is important for diagnosis and therapy to be able to initiate a sufficient immune response. The process in accordance with the invention, on the other hand, permits the provision of a large quantity of tumor-specific antigens in the form of a culture of the transformed cells, which can be reproduced at discretion.

To separate the blood into its components, one uses a suitable device for this purpose, such as is used in the so-called apherese process. In contrast to the usual separation processes, in which a large amount of whole blood is taken from the patient and is separated into fractions using a centrifuge, in the apherese process, the separation device is connected via lines directly with the blood stream of the patient, and thus in principle it is rather similar to a dialysis process. In this way it becomes possible to separate the blood taken from the patient, to separate the desired fraction and then immediately to return the other blood components to the patient. Therefore apherese processes permit the quasi-continuous removal of predetermined blood fractions in high quantities, without burdening the patient. Therefore one speaks with respect to the apheretic collection of blood plasma of "plasmapheresis", and as regards the collection of leucocytes of "leucapheresis" etc. (U.S. Pat. No. 5,112,298, U.S. Pat. No. 5,147,290).

Until now, it had been assumed that the apherese processes, which are known per se, are only suitable for the separation of white blood corpuscles which are circulating constantly and peripherally in any case in the circulatory system and other blood components which are present in relatively large amounts. Now the inventors have surprisingly found that the extracted and transformed cells of a primary tumor are also enriched in a particular cell fraction.

The separation of the blood components is performed advantageously in a centrifuge with a rotating container, such as is normally also used for the apheretic lymphocyte separation of blood plasma, of erythrocytes and other blood components without chemical density gradients and subsequent enrichment (e.g. Haemonetics V50-1 (the so-called "Latham-Bowl"), commercially available by Haemonetics, Inc., U.S.A.). The centrifuge itself has a capacity of about 100 to 200 ml of blood.

Such centrifuges have until now been used, for example, in a process for the reduction of the lymphocyte population in the case of patients having lymphocyte leucaemia in combination with an extracorporal radiation process (EP-A 0 030 358). For this purpose blood is taken from the patients and it is irradiated in the presence of a photo-reactive chemical compound, such as for example a psoralen derivate, which was previously administered orally or was administered to the blood after extraction with ultraviolet light. The psoralen intercalates with the DNA of the cells and is capable of reacting after photo-activation with the DNA and thereby eliminating oncogens. Then the irradiated blood is supplied to the patient again.

The inventive process makes it possible to separate protectively from the blood only the fraction with the transformed and enriched cells therein and the leucocytes and/or lymphocytes which under certain circumstances are still contained, while the other blood components are returned to the patient. For preference, this is done continuously in one work process. In this way the stress on the patient is kept as low as possible, and on the other hand it is possible to isolate in a short time sufficient amounts of transformed cancer cells, which can then be correspondingly further processed.

Before the supply of blood, the centrifuge may be filled with a pharmaceutically acceptable, isotonic solution which is supplemented with a clot-inhibiting agent, for example heparin, and usually 1000 to 2000 units are sufficient for this purpose. For the separation of transformed cells from the blood stream, via a suitable bypass mechanism mounted on the centrifuge outlet, a discretionary number of white blood corpuscles is extracted with transformed cells mixed among them, wherein the expert is in a position without difficulty to identify the leucocyte fraction:

On the appearance of a white band which is clearly distinguished from the red erythrocytes, the bypass of the centrifuge is opened and about 40 ml of the white blood corpuscles are removed in the case of a centrifuge having a capacity of 120 ml. The red blood corpuscles, the plasma and the other blood components are then returned to the body.

The fraction which is enriched with the transformed cells, which contains leucocytes and/or lymphocytes (hereinafter briefly named the "cell fraction") is transferred to a culture solution. For culturing the transformed cells, every basic cell culture medium can be used which contains a carbon and nitrogen source as well as further necessary inorganic and organic components, such as vitamins, amino acid and trace elements. Preferably media which ere on the market, such as e.g. RPMI 1640 medium are supplemented optionally with a supplement such as foetal calf serum. The culture conditions are adjusted in accordance with the producer information, normally standard conditions of 5% $CO_2$, 37° C. and 95% air humidity are used.

In the case of a small primary tumor, which possibly has not yet even been diagnosed or localized or which is still in the stage before metastase formation, only extremely small amounts of transformed cells circulate in the blood. The addition of macrophage inhibiting peptide to the cell fraction prevents the few transformed cells in the large surplus of lymphocytes from being destroyed by macrophages. Additionally, the addition of B- and T-cell-specific antibodies (CD-8-, CD-25-, interleucine and interferon-specific antibodies) inhibits the production of the lymphocytes which finally die out. By the known cell sorting process, alternatively the leucocytes, lymphocytes and other disturbing cells can be separated from the cell fraction. The batches are distributed on wells of microtiter plates and after about four days, the clones of the transformed cells are clearly visible. The transformed cells can be differentiated clearly on the basis of their morphology from possibly still existing lymphocytes and they are very similar to primary tumor cells. After about one week, enough transformed cells are available for the subsequent immunization. The clones can also be frozen for use at a later date.

The cancer cells can De returned to the body in modified non-pathogenic form as immunogen. For this purpose, for example, isolated membrane fractions which still carry the tumor antigens can be used. For this purpose another alien organism, e.g. mouse, rabbit or goat, or the same organism from which the antigens were extracted is immunized by these antigens. The polycolonal or monoclonal antibodies which are produced by conventional methods can be used for diagnosis or for therapy.

According to a preferred embodiment of the invention the cultivated cancer cells are used to stimulate isolated B-lymphocytes from the same organism. Advantageously one uses for this purpose the so-called in vitro immunization, i.e. the B-lymphocytes are brought into contact outside the body with the transformed cells in a suitable medium. From the B-lymphocytes which are thus stimulated, one produces hybridoma cell clones which are in a position to secrete permanently antibodies. Apart from the hybridoma technology, the immortalization of the B-lymphocytes with Epstein-Barr viruses is also possible. Therefore the invention imitates the immune system of the body itself in a manner which is technically controllable.

In an embodiment of the invention, the transformed cells which are expanded in culture are brought into contact at a given point in time, but preferably as soon as possible after removal, i.e. after about 8 to 10 days, with endogenous B-lymphocytes of the patient. Because for the isolation of B-lymphocytes, only about 50 ml of blood are necessary, they can be isolated by centrifugation from whole blood in a density gradient, e.g. a ficoll gradient. The extraction of the B-lymphocytes, however, is performed advantageously using the separation device which is used in accordance with the invention as lymphocyte apherese. Particular preference is given to the process steps, i.e. the application of the cancer cell culture and the isolation of the B-lymphocytes are coordinated with each other so that an in vitro immunization can take place at the earliest possible time after cell extraction, i.e. after about 8 to 10 days.

For the in vitro immunization, the entire cell fraction can be used (T- and B-lymphocytes), because only the stimulated B-lymphocytes secrete the antibodies, wherein the cell fraction and the transformed cells are used in a ratio, based on the number of cells, preferably from 100:1 to 1:1 and with special preference for the ratio of about 10:1. By the addition of interleucines such as IL-2, IL-4, IL-5, IL-6 and gamma interferon, the stimulation of the antibody-forming cells is favoured. The concentration of these adjuvants in the immunization batch is respectively 0.1 to 10 mM, preferably about 1 mM.

For unlimited expansion, the stimulated B-lymphocytes must be immortalized. This can preferably be done by transformation of the B-lymphocytes with Epstein-Barr viruses, by analogy with the process as described in the German patent DE 39 28 769 C2. For the production of large quantities of antibodies preference is given to the preparation of a hybridoma culture. For the fusion with the B-cells, depending on the donor organism, species-specific myelomacells are used. In the case of human beings, the myeloma cell line U-266 has been found to be especially suitable for this purpose. The B-cells are combined with the myeloma cells in the optimal ratio of 1:1. Additives such as polyethylene glycol can be added to support the cell fusion. Then the batch is disseminated for selection on hybridoma clones on wells of microtiter plates and the culture supernatant is tested for antibodies. The culture conditions are the usual ones for hybridoma cultures.

By epitope screening, hybridoma clones are selected which recognize various antigens,i.e. determinants on the surface of the transformed cell, and the specificity of the antibodies is verified. The hybridoma cell lines obtained in this way can be further reproduced for the extraction of antibodies and/or can be frozen for later use.

The antibodies are isolated by conventional processes from the culture supernatant and are purified with conventional protein purification methods, such as ammonium sulfate precipitation, gel chromatography, ion exchange chromatography, affinity chromatography and/or FPLC and electro-phoretic processes as far as possible to homogeneity.

The extracorporal in vitro immunization is performed without passage into alien organisms and supplies large amounts of antibodies, which are specific for the special tumor of the donor individual and thus are optimally suitable for use for its diagnosis and for counter-action in this special individual. On the other hand, the antibodies originate from B-lymphocytes, which were also taken from the same individual. These antibodies are therefore "endogenous" proteins, although they were prepared outside the body, which after application in the organism do not initiate any immune response directed against it, which otherwise could lead to their rapid decomposition and therefore to reduced therapeutical activity.

The antibodies prepared in accordance with the inventive process comprise all the subclasses such as IgG, IgM and IgE, with preference given to antibodies of the IgG type. The antibodies can furthermore be modified chemically or enzymatically, as long as their physiological activity, i.e. recognition and binding on the cancer cell-specific antigen determinants, remains.

In accordance with the conventional glutaraldehyde process, immunotoxins, such as e.g. ricin or diphtheria toxin, can be coupled with the antibodies. Furthermore, the antibodies can be labelled with radioactive substances, e.g. $^{125}I$ or marker enzymes for a RIA or ELISA.

In a preferred embodiment, the antibodies are used without further modifications to prepare a pharmaceutical, in which in a pharmaceutical composition one or more monoclonal antibody types may be contained, which are respectively directed against a defined epitope.

After administration to a patient, they are in a position to bind on deposited tumor cells and in this way to entice macrophages or endogenous killer cells, which then destroy the cancer cells for their part.

The antibodies are administered in a pharmaceutically acceptable formulation, together with the conventional carriers, diluents, stabilizers and optionally other ancillary substances. The pharmaceutical may be present in any suitable formulation, preferably in the form of a solution which can be injected intravenously, intramuscularly or subcutaneously. With special preference, the antibodies are lyophilized after their extraction, filled in a unit dose and sealed. Shortly before use, antibodies are dissolved or suspended with a carrier solution suitable for the injection. The carrier solution, normally a sterile, buffered aqueous solution can be enclosed in its own ampule, together with the lyophilized antibodies in a pharmaceutical packing. The physician will select a suitable dose and form of administration depending on the age and state of the patient, on the type of the tumor and on the gravity of the disease.

For the preparation of a pharmaceutical for counteracting tumors, preferably the property of an antibody can be used, i.e. to recognize its corresponding antigen with high specificity and to bind thereon. An active ingredient which is connected covalently with the antibody in a suitable manner, i.e. not over the area which is important for antigen recognition, can thus be directly transported via antibodies as the transport vehicle to the desired location, in order to develop its activity there alone and not unspecifically distributed in the organism. By coupling immunotoxins, e.g. ricin, or radio-therapeutic agents to these monoclonal antibodies in accordance with the processes known per se, the tumor cells can thereby be destroyed.

By the administration of these modified and/or unmodified antibodies, tumor cells can be detected and destroyed which were adhering to the endothelium. Furthermore, this process also permits the destruction of possibly non-operable solid tumor shares or of the total solid tumor, such as metastases which have already formed. After the operation, the administration of antibodies can be performed prophylactically for a corresponding period, in order to prevent the resettlement of circulating transformed cells or the appearance of metastases. Administration can also take place together with other conventional pharmaceuticals for the treatment of tumors, such as cytostatic agents or the like and the accompanying therapeutic measures, irradiation etc.

For diagnostic purposes, these antibodies can be coupled on radioactive or non-radioactive markers, and can be used in vivo and in vitro for the search for and marking of tumor cells. The high selectivity and binding affinity of the antibodies permits by simple means the quantitative and qualitative determination of the number of transformed cells in the blood stream of a patient in an in vitro test system. Thanks to the sensitivity of such a test, with which only a few transformed cells can be proven in a sample, only a little blood has to be taken from the patient, and due to the constant availability of the antibodies, the test can be carried out regularly over a long period for diagnosis.

It is an important characteristic of the invention that the products extracted in accordance with this process, such as e.g. the culture of the transformed cells, the hybridoma culture and the antibodies, are highly specific for the organism concerned. This means for the antibodies that they differ in particular with respect to their non-antigen recognizing zones from those of another organism, e.g. from another patient who has the same tumor disease, more or less strongly in their structure. On the other hand, the antibodies are practically endogenous for the respected individual and are not recognized by the immune system as "alien". The process in accordance with the invention makes it possible within a relatively short period and with acceptable expenditure to produce for a particular patient, e.g. by the use of the antibody specific to the individual, a pharmaceutical or diagnostic agent specially adapted to him, which apart from its specific activity is also distinguished by high compatibility.

However, this does not mean that the use of antibodies, which were prepared from and for a certain individual, would be excluded in principle for other individuals. It is known that human antibodies within the same species are more compatible than chimetic or even animal antibodies. If the antibodies are used for in vitro diagnosis, the compatibility in any case plays no part. Therefore in the case of a patient for whom there is the suspicion of a certain tumor disease or such a disease has already been diagnosed, initially and experimentally antibodies obtained from another patient will be used. If they respond in the desired manner and are suitably compatible, it is no longer necessary to prepare his own antibodies for this patient, as described above.

Should it nevertheless come to incompatibility reactions and if one is aware of the type of the primary tumor, it is enough in many cases to stimulate the endogenous B-lymphocytes of the patient with cultures of transformed cells of the same cancer type which have already been isolated and reproduced from other individuals using the inventive process. The antibodies produced thereby, are highly compatible because they are "quasi-endogenous" to the body. It is only if they should not have sufficient specificity for the individual cancer of the patient that it becomes necessary to carry out the complete isolation, cultivation and immunization process in accordance with the present invention.

Therefore the present invention constitutes a graduated and individually adaptable process for the production of an agent which can be used for diagnosis and/or therapy of a particular cancer disease in a plurality of individuals of a defined mammal species.

In a preferred embodiment of the inventive process, various hybridoma cell lines from one or several patients having the same tumor are established and selected in accordance with those monoclonal antibodies which differentiate the specific antigen determinants on the cancer cells. In this way it can be determined whether on transformed cells which were isolated from different patients with the same tumor disease, identical determinants occur. These antibodies can then be used for diagnosis and possibly for therapy as well in the case of other patients, without it first being necessary to carry out an immunization with endogenous B-lymphocytes.

The antibodies can be formulated in pharmaceutical compositions in modified and unmodified form in accordance with the conventional methods, as described above.

The simple, rapid and economical practicability of the process permits its use in checking for cancer or early recognition, without a tumor having been diagnosed already. It is also suitable all the more for investigation on suspicion of cancer in routine work for the presence of transformed cells or for determining in the case of the presence of a solid organ tumor which is discernible by X-rays whether the tumor has already distributed malign cells in the circulatory system or not. Furthermore, in the case of a doubtful finding (transformed or non-transformed cells) an investigation can be made for the presence of peripherally circulating transformed cells. For this purpose, the antibodies and/or their especially suitable derivates are made available in a diagnosis kit, preferably for an ELISA.

The process above is not only applicable in the field of human medicine, but also to mammals in general in veterinary medicine and to related scientific disciplines. The exemplary reference to a human patient as a representative of a laving individual in the specification should therefore not be restrictively interpreted.

With the inventive process it is possible to extract safely and without the addition of chemicals or other adjuvants transformed cells for diagnostic and therapeutic purposes from a living organism of human beings and animals. The process permits the extraction of a large number of tumor cells circulating in the system. Thereby the tumor stress, which normally contributes to the metastastatic process, is reduced.

The inventive process provides, in particular, the following advantages:

- The extraction of the transformed cells can be carried out extremely protectively for the organism, i.e. there is no increased release of such cells in the blood stream.
- The isolation process permits the number of peripheral transformed cells to be very sharply reduced in the blood stream and therefore it reduces the risk of a metastase formation, e.g. after an operation to remove the primary tumor.
- The optimal coordination of the individual process steps makes possible the generation of polyclonal or monoclonal antibodies in a relatively short time and with low costs.
- The antibodies extracted are individually specific, i.e. they are not alien bodies for the organism concerned. There is neither an imcompatibility reaction, nor are the antibodies excessively swiftly decomposed in contrast to other alien proteins, whereby their efficiency is substantially increased.
- The antibodies are tumor-specific, i.e. they recognize with high selectivity the specific antigens of the special tumor from the individual concerned, the antigen recognition of transformed cells from other individuals, however, is not excluded.
- The pharmaceutical active ingredients coupled with the antibodies develop their activity not unspecifically distributed over the organism, but substantially only at the desired location (cell-targeting); undesirable side effects are therefore largely avoided.
- The pharmaceutical which is prepared from the antibodies can be used not only against the transformed cells circulating in the blood stream, but also to counter-act the primary tumor and possibly already formed metastases.
- The pharmaceutical prepared from the antibodies is extracted from endogenous resources, while the risk of alien infections, e.g. by hepatitis or by AIDS is excluded.
- The extraction of the antibodies which are tumor-specific for the individual patient is possible with acceptable expenditure, so that they can be used not only for the preparation of patient-specific pharmaceuticals, but also for early detection, diagnosis or post-treatment after operations.
- Use of the antibodies extracted from an individual organism for other organisms than the "producer organism" is possible.

The following examples serve to illustrate the inventive process.

MATERIALS AND METHODS

1. Instruments Required 1.1. Cell Culture a sterile work bench, $CO_2$ incubator, incubator, hot plate, fluorescence microscope, phase contrast microscope, centrifuge for variable rotors, refrigerators (4°, −20°, −80° C.), liquid nitrogen, autoclave 1.2. ELISA microplate photometer, pipette, 8-channel 1.3. Purification of the Monoclonal Antibodies

FPLC, HPLC 1.4. Biochemical Analysis

IEF instrument, midget system, electroblot, 2-dimensional gel electrophoresis, transformer 1.5. Apheretic Device Haemonetics V50-1 (Latham-Bowl), capacity 120 ml, with bypass, Haemonetics, Inc., U.S.A.

2. Reagents 2.1. Tissue Culture medium RPMI 1640, foetal calf serum, L-glutamine Na-pyruvate, phosphate buffer solution (PBS) pH 7.0, 20 mM, HAT medium 2.2 Monoclonal Antibodies anti-CD 8, anti-CD 25, anti-IL-2, anti-IFN gamma (all obtainable from Serva)

recombinant IL-2, IL-4, IL-5, IL-6, IFN gamma (all obtainable from Serva)

macrophage-inhibiting peptide (Thr-Lys-Pro, tuftsin-fragment 1–3), (obtainable from Sigma)

2.3. Cell Fusion

50% polyethylene glycol 1500 in HEPES buffer, 75 mM, (50% weight/volume)

3. Process 3.1. Isolation and Reproduction of Cancer Cells by Means of Aphoresis Using a Haemonetics V50 centrifuge which is provided with a bypass, in the case of two patients with different types of tumors (prostate carcinoma, melanoma) a cell fraction of respectively 120 ml blood was extracted in accordance with the process described above.

The histological stage of the patients was known from a previous operation.

$2,4 \cdot 10^9$ white blood cells from cell fraction were taken in a tube with cell culture medium (RPMI 1640) and investigated as follows.

The cells were cultivated overnight under the standard conditions (37° C., 5% $CO_2$, 95% air humidity). As the medium, RPMI 1640 with 10% of foetal calf serum was used with the addition of B- and T-cell-specific antibodies (CD 8-, CD 25-, IL-2- and IFN gamma-specific antibodies) and with the addition of macrophage-inhibiting peptide in the following concentrations:

| | |
|---|---|
| anti-IFN: | 100 µg/500 ml medium |
| anti-CD 25: | 100 µg/500 ml medium |
| anti-CD 8: | 1 mg/500 ml medium |
| macrophage-inhibiting peptide (MIP): | 50 mg/500 ml medium |

The batch was distributed on microtiter plates with respectively 200,000 cells in 100 µl per well. On the fourth day after inoculation, the cells were fed with respectively 100 µl medium (without antibody or MIP additive). During the entire culture period, it was constantly gassed with 5% $CO_2$ at 37° C. The cancer cells were clearly visible after division as clones after four days in the phase contrast microscope.

For control purposes, the same batch was depleted in the medium without the addition of antibodies and macrophage-inhibiting peptide, whereby the cancer cells were first recognizable after three weeks in the phase contrast microscope as clones. A clone of the batch with added antibodies and macrophage-inhibiting peptide was removed and reproduced, until a cell number of $10^8$ was obtained. Further clones were reproduced and frozen.

3.2. Immunization

The white blood cells had to be caused to secrete antibodies against cancer cell specific antigens. For this purpose in one of the apheretic cycles, $10^9$ white blood cells were removed, combined with $10^8$ cancer cells and incubated for four days in 100 ml of human heparinized plasma in roller culture at 37° C., 5% $CO_2$. By the addition of IL-2, IL-4, IL-5, IL-6 and IFN gamma, the maturation to antibody-forming cells was stimulated. The concentrations amounted respectively to 100 µg per 100 ml of the immunization batch.

3.3. Cell Fusion

The B-lymphocytes were separated by means of a FACS from the other cells. Some days before fusion, the human myeloma cells (U266) were kept in a cell density of $3 \cdot 10^5$ cells/ml in the logarithmic growth phase. The myeloma cells were harvested simultaneously with the B-lymphocytes and were washed three times in PBS. Four fusion batches were prepared, wherein respectively $5 \cdot 10^7$ myeloma cells were centrifuged together with $5 \cdot 10^7$ B-lymphocytes and then were fusioned with respectively 1 ml 50% polyethylene glycol in HEPES. Then the slow addition of 10 ml RPMI 1640 followed. The fusion batch was washed in RPMI 1640, was centrifuged for two minutes at 200·g at room temperature, respectively accepted in 50 ml HAT medium and seeded out at respectively 0.1 ml per well in 96 well microtiter plates. Human macrophages in the number of $10^4$ per well were used as the feeder cells.

3.4. Screening

The culture supernatant of the hybridoma cells was tested with an ELISA for antibodies. A cell ELISA was established for this purpose. Cancer cells were coated by suitable methods on the plastic surface of the microtiter plates, and antibodies possibly binding on them were detected by a second antibody.

ELISA

In the first screening after diffusion a search was made for clones which secrete immunoglobulin.

1. Incubation of culture supernatant in microtiter plates at respectively 100 µl per well overnight at 4° C.
2. Washing three times with PBS
3. Blocking with albumin or blotto, 2 h, 37° C.
4. Washing three times with PBS
5. Incubation with specific antibodies against human immunoglobulin, 2 h at 37° C.
6. Incubation with an enzyme-conjugated second antibody (peroxidase or alkaline phosphatase) 1 h at 37° C.
7. Developing by the addition of substrate and measurement in the read-out instrument The positive clones are tested for antibodies specific to cancer cells. For this purpose a cell ELISA was established:
1. Preparation of a poly-L-lysine solution of 1 mg/ml in distilled water
2. Incubation of the microtiter plates with poly-L-lysine for 15 minutes
3. Washing with water. Storage at room temperature after drying
4. Washing the cells twice in suspension in PBS, centrifugation at 400·g
5. Resuspension of the cell pellets in PBS at $10^5$ cells per ml. Filling the microtiter plates, incubation for 10 minutes at room temperature.
Fixation Respectively 200 μl of an acetone/methanol mixture (50/50% by volume) were poured into the wells of the microtiter plates and incubated for 2 minutes at room temperature. Then washing was performed once with PBS.

The further steps were implemented as in the first screening.

3.5. Biochemical Analysis

Monoclonal antibodies were analysed direct from the culture supernatant. The subclasses of the light and of the heavy chain were determined by means of a subclass test kit in ELISA. Using iso-electric focussing, the monoclonality of the antibodies could be ascertained (Hoffmann et al., Human Genetics, Springer Verlag, 1990, 84, 137 to 146).

3.6. Epitope Screening

Cancer cells were cultivated, $10^7$ cells were removed, washed three times with PBS and divided into two fractions. One fraction was homogenized and analysed in the native gel-electrophoresis (pH 8.8, 9% acrylamide in the separation gel and 3% acrylamide in the collector gel), the others were denatured (urea, SDS) and were separated with monodimensional and two-dimensional gel-electrophoresis (Waldinger et al., Electrophoresis, 1986). Detection of the subsequent western blot was carried out with the culture supernatant. The band and/or the spot which was recognized was extracted and sequenced and thus the tumor-specific antigen was identified. Samples of other tissues and white blood cells were used as the control (E. Harlowe, D. Lane, Antibodies, A Laboratory Manual, Cold Spring Harbor Laboratory, 1988; D. Baron, U. Hartlaub, Humane monoklonale Antikörper, Gustav Fischer Verlag, Stuttgart, New 1987).

4. Results

In both cases (prostate carcinoma, melanoma) after four days clones of transformed cells were already visible in the phase contrast in about 30% of the wells of the cell culture plates.

The cell fraction of a patient with a non-malign disease (auto-immune regulation disturbance of the lymphocytes) was used as the control, in which the white blood corpuscles had to be treated outside the body for other reasons. In this case, no cell divisions were found.

By analogy, the following transformed cell lines were isolated and hybridoma cultures were produced from them, which secreted the corresponding antibodies:
breast carcinoma
B-cell lymphoma
bronchial carcinoma
kidney adeno carcinoma 5. Deposit of the Cancer Cell and Hybridoma Cell Lines The following cultures of transformed cells (cancer cell lines) were produced and the corresponding hybridoma cell lines were produced from them:

| Tumor | cancer cell line (laboratory code) | DSM-accession no. | hybridoma cell line (laboratory code) | DSM-accession no. |
|---|---|---|---|---|
| breast carcinoma | DWM 3 | * | 2G3 | * |
| B-cell-lymphoma | HAB 1 | * | 2D9 | * |
| bronchial-carcinoma | SB 1 | * | 5F6 | * |
| kidney-adenocarcinoma | HNA 3 | * | 9G2 | * |
| prostate-carcinoma | SB 2 | * | 369 P | * |
| melanoma | LWM 1 | * | 4E6 | * |

*not yet known at date of application

The hybridoma cell lines were stable and secreted 5–7 μg antibodies per $10^6$ cells in 24 hours (the literature states for human hybridoma an average value of 1–10 μg antibodies per $10^6$ cells in 24 hours).

The cancer cell lines and the hybridoma cell lines were deposited in accordnce with the Budapest agreement on Aug. 17, 1993, at the Deutsche Sammlung für Mikroorganismen, DSM, Mascheroder Weg 1b, 38 124 Braunschweig, Federal Republic of Germany.

What is claimed is:

1. A process for the isolation of transformed cells from the bloodstream of an individual suspected of having a solid tumor comprising the steps of:

withdrawing blood from an organism; and separating from other blood components, through use of a cell separation system that does not kill the cellular components of the blood, a fraction of the blood containing at least one cell type selected from the group consisting of leucocytes and lymphocytes wherein said at least one cell type is enriched with transformed cells.

2. The process of claim 1 wherein whole blood is (1) continuously withdrawn from an organism, (2) conducted through an apheretic device, which extracts the cell fraction containing said at least one cell type which is enriched with transformed cells, and (3) the other blood components are returned to the organism.

3. The process of claim 1 wherein the transformed cells are reproduced in an environment which inhibits the growth or function of said at least one cell type.

4. The process of claim 3 wherein the growth or function of said at least one cell type is inhibited by the addition of at least one of (1) macrophage inhibiting peptide; (2) B-lymphocyte specific antibodies; or (3) T-cell specific antibodies.

5. The process of claim 1 wherein the transformed cells are selected from the group consisting of (1) breast carcinoma; (2) B-cell lymphoma; (3) kidney adeno carcinoma; (4) bronchial carcinoma; (5) prostate carcinoma; and (6) melanoma.

6. The process of claim 1 that additionally includes reproducing the transformed cells in vitro.

7. The process of claim 1 wherein the cell separation system is an apheretic device.

8. A method for determining the presence of transformed cells in the bloodstream of an individual suspected of having a solid tumor comprising the steps of:

withdrawing blood from an organism;

separating from other blood components, through use of a cell separation system that does not kill the cellular components of the blood, a fraction of the blood containing at least one cell type selected from the group consisting of leucocytes and lymphocytes wherein said at least one cell type is enriched with transformed cells; and screening said fraction of the blood with antibodies specific to tumor cell markers to identify the presence of transformed cells in said fraction of the blood.

9. The method of claim 8 further comprising, before said screening, the step of culturing said fraction of the blood to allow the transformed cells, if present, to overgrow the cells of said at least one cell type.

10. The method of claim 8 wherein said antibodies are monoclonal.

11. The method of claim 8 wherein said antibodies are polyclonal.

12. A method for determining the presence of transformed cells in the bloodstream of an individual suspected of having solid tumor comprising the steps of:

withdrawing blood from an organism;

separating from other blood components, through use of a cell separation system that does not kill the cellular components of the blood, a fraction of the blood containing at least one cell type selected from the group consisting of leucocytes and lymphocytes wherein said at least one cell type is enriched with transformed cells; and culturing said fraction of the blood to allow the transformed cells, if present, to overgrow the cells of said at least one cell type.

* * * * *